United States Patent
Wolf et al.

Patent Number: 5,449,519
Date of Patent: Sep. 12, 1995

[54] COSMETIC COMPOSITIONS HAVING KERATOLYTIC AND ANTI-ACNE ACTIVITY

[75] Inventors: Barbara A. Wolf, Scarsdale, N.Y.; Florence Snyder, Sayreville, N.J.

[73] Assignee: Revlon Consumer Products Corporation, New York, N.Y.

[21] Appl. No.: 288,098

[22] Filed: Aug. 9, 1994

[51] Int. Cl.⁶ .................................................. A61K 6/00
[52] U.S. Cl. ................................ 424/401; 424/70.8; 424/71; 424/70.12
[58] Field of Search ........................ 424/401, 70.8, 71

[56] References Cited

U.S. PATENT DOCUMENTS

| | | | |
|---|---|---|---|
| 2,614,962 | 10/1952 | Elson | 167/61 |
| 3,296,078 | 1/1967 | Kaye | 167/92 |
| 3,560,614 | 2/1971 | Embring | 424/234 |
| 4,318,907 | 3/1982 | Kligman | 424/230 |
| 4,355,028 | 10/1982 | Kligman | 424/230 |
| 4,514,385 | 4/1985 | Damani | 424/81 |
| 4,536,399 | 8/1985 | Flynn | 514/63 |
| 4,593,046 | 6/1986 | Gruber | 514/717 |
| 4,608,370 | 8/1986 | Aronsohn | 514/159 |
| 4,608,392 | 8/1986 | Jacquet et al. | 514/844 |
| 4,800,197 | 1/1989 | Kowcz | 514/162 |
| 4,895,727 | 1/1990 | Allen | 424/642 |
| 4,963,591 | 10/1990 | Fourman | 514/944 |
| 5,085,856 | 2/1992 | Dunphy | 424/401 |
| 5,122,370 | 6/1992 | Merianos et al. | 424/78.05 |
| 5,139,771 | 8/1992 | Gerstein | 424/401 |
| 5,145,685 | 9/1992 | Carmody | 424/484 |

OTHER PUBLICATIONS

Glyacid and Protacid, Bioetica brochure 1993, Jul.

*Primary Examiner*—Thurman K. Page
*Assistant Examiner*—William E. Bentson, Jr.
*Attorney, Agent, or Firm*—Julie Blackburn

[57] ABSTRACT

A cosmetically acceptable composition with anti-ache or keratolytic activity comprising: 0.01 to 25% by weight of a keratolytic compound complexed to a carrier molecule, 75-99.95 % by weight of a diluent.

20 Claims, No Drawings

COSMETIC COMPOSITIONS HAVING KERATOLYTIC AND ANTI-ACNE ACTIVITY

TECHNICAL FIELD

The invention is in the field of cosmetic compositions having keratolytic and anti-acne activity.

BACKGROUND OF THE INVENTION

*Acne vulgaris* is reported to be the most common skin disease, affecting approximately eighty percent of the teenage population, and in some cases persisting into the third and fourth decades of life. The pathology of ache is believed to first involve the formation of comedones, which are solid, horny masses of tightly packed keratinized cells which plug follicles. These comedone plugs are first white when formed (whiteheads), but through continued growth and deposition of melanin become blackheads. As the comedo enlarges through continued accumulation of keratinized cells, pressure builds up within the follicles and they eventually rupture, dumping the contents (consisting of horny material, sebum, and bacteria) into the skin. This provokes an inflammatory response; when the rupture is small pustules or pimples develop, and when the follicle completely ruptures cystic nodules result.

It is well known that *acne vulgaris* can be treated by application of agents which dry and peel the skin to remove keratinous plugs. Well known keratolytic agents are sulfur, resorcinol, benzoyl peroxide, salicylic acid, and hexachlorophene. Benzoyl peroxide is an antimicrobial agent which effectively suppresses the ache bacillus Propionibacteritm aches, an organism which has an important causal role in ache. In addition to being an effective keratolytic agent, salicylic acid also interferes with the formation of blackheads, whiteheads, and the horny masses which clog follicles.

Salicylic acid, benzoyl peroxide, and resorcinol have been incorporated into various anti-acne preparations for years. However, due to the acidic nature of these ingredients, they often exert undesireable effects on the carrier formulation. Salicylic acid, for example, is not water soluble; it can only be solubilized in oils or alcohol. When salicylic acid is incorporated into these preparations at a pH of above 3, it converts to salicylate and causes stability problems in the formulation. Also, salicylic acid is light sensitive above a certain pH. Make-ups made with salicylic acid are known to fade on exposure to light and can be slightly irritating in sensitive skinned individuals who are prone to skin irritations. There is therefore a need for anti-acne preparations having improved stability and aesthetic properties.

SUMMARY OF THE INVENTION

The invention is directed to a cosmetically acceptable composition with anti-keratolytic activity comprising:
  0.01 to 25% by weight of a keratolytic compound complexed to a carrier molecule, 75–99.99% by weight of a diluent.

The invention is also directed to a method for treating *acne vulgaris* comprising:
  a) complexing a keratolytic compound to a carrier molecule,
  b) adding an effective amount of said complex of (a) to a cosmetically acceptable diluent.

DETAILED DESCRIPTION

It has most unexpectedly been discovered that if keratolytic compounds, particularly those known to also have anti-ache activity are bound to a certain carrier molecules, the resulting complex will remain stable in cosmetic preparations. When the complex is applied to the skin in a cosmetic composition, the keratolytic con, pound becomes disassociated from the carrier molecule on the skin and is absorbed into the skin to provide the desired anti-acne effect. In the case of salicylic acid, the complexation of the salicylic acid in the cosmetic preparation is believed to prevent the conversion of salicylic acid to salicylate, and enhances the stability and aesthetics of the cosmetic preparation. The various ingredients of the cosmetically acceptable composition according to the invention are described in more detail below.

The term "keratolytic compound" means a chemical compound having keratolytic and/or anti-acne activity.

THE ANTI-ACNE ACTIVE

The keratolytic compounds which are suitable for use with the invention contain an acid group or tend to be acidic and are capable of binding with the free amino group of a protein or polymer. The binding may be ionic, covalent, or through Van Der Waals forces. Anti-acne ingredients capable of forming ionic bonds include salicylic acid and resorcinol. Benzoyl peroxide will bond to carrier molecules, or bind through Van der Waals forces.

THE CARRIER MOLECULE

A wide variety of carrier molecules are suitable, so long as the carrier molecule possesses at least one free amino group.

Animal protein or peptides such as collagen, placental proteins, serum proteins, amylase, casein, urease, keratin, silk, hydrolyzed animal protein, albumin, etc. are well known in the cosmetic art and are capable of ionic binding to the keratolytic compound. The preferred carrier molecule comprises hydrolyzed animal protein, collagen, or keratin.

Vegetable or plant proteins or polyamino saccharides containing free amino groups are also suitable, such as soya, corn, sweet corn, lupin, wheat gluten, guar, oat, extensins, hydrolyzed vegetable proteins, and so on, as well as polymers of amino sugars such as chitosan. The preferred carrier molecule in this category comprises hydrolyzed vegetable protein, or extensins.

A wide variety of synthetic polymers have free amine groups are also suitable as the carrier molecule. Particularly desireable are branched polyamidoamines as set forth in U.S. Pat. Nos. 4,435,548, 4,737,550, 4,871,779, 4,857,599, 4,713,975, 4,694,064, 4,690,985, 4,631,337, 4,599,400, 4,587,329, 4,568,737, 4,558,120, and 4,507,466 which are hereby incorporated by reference. These patents disclose and claim dense star-type polymers with dendritic branches which have highly reactive substitutent groups.

Other synthetic polymers such as polyamides, polyanilines, polyureas, polyurethanes, and contain at least one free amino group and would be suitable carrier molecules. Certain other polymers with free hydroxyl groups, such as polyvinyl alcohols, poly (2-HEMA) and poly (2-HPMA) will bind by Van der Waals forces.

COMPLEXATION OF THE KERATOLYTIC COMPOUND TO THE CARRIER MOLECULE

The keratolytic compound is attached to the carrier molecule employing a variety of chemical reactions depending on the carrier molecule and the anti-acne active used. The term "complex" refers to the keratolytic compound complexed or bound to the carrier molecule.

Salicylic acid and resorcinol have free acid groups which will ionically bond to the tree amino groups of proteins or polymers. Binding of the salicylic acid to vegetable or animal proteins is achieved by simply combining approximately equal parts of both ingredients in suitable vessel. The salicylic acid will react with the free amino groups on the carrier molecule to form a complex. Sometimes a slight degree of heat will hasten the reaction, or the addition of small amounts of acid such as hydrochloric acid. Salicylic acid may also be complexed to various carriers such as hydrolyzed vegetable proteins as described in French patent no. 2667072 which is hereby incorporated by reference. In particular, a concentrated solution of salicylic acid in alcohol is mixed with a concentrated solution of hydrolyzed vegetable protein in water. The resulting dispersion is mixed under shear or alternatively by ultrasonic agitation. Depending on the type of protein selected, the complex may precipitate upon forming or may be recovered by vacuum distillation or lyophilization by method known to those skilled in the art. The resulting powder effectively solubilizes the complexed salicylic acid which can be recovered and analyzed as salicylic acid by traditional wet chemistry. Alternatively, the salicylic acid can be rendered more water soluble by using a metal alkali salt such as sodium or potassium and complexing at a pH of 5.5 to 6.5. The powdered hydrolyzed protein is then added to a dispersion of the salicylate in a buffered water solution.

Salicylic acid can be complexed with the dendritic polymers disclosed herein. Dendritic polymers are constructed to vary in size and shape depending upon the initiator and the molecule used to grow the shell. Of particular interest are the starburst dendrimers of the polyamidoamine (PAMAM) type because the outer shell is covered with amino groups which will complex with salicylic acid. As in example one, the starting point can be either a water dispersion of dendrimer to which is added salicylic acid in a volatile solvent, or a solution of salicylate at pH 5.5 to 6.5 to which is added crystals of dendrimers. The size of the dendrimer will allow multiple sites for complexation, but not so large that solubility in water is hindered. Dendrimers having 1–10 generations are ideal. Since the dendrimers can develop holes or irregularities, some salicylic acid may be sequestered within the shell as well as complexed to the surface. As with the protein, a high complexation ratio is desireable.

Salicylic acid will also bind to synthetic polymers which have free amino groups in a manner similar to binding to proteins. Such polymers include: polyamides $-(R-CO-NH)_n-$, polyanilines $-(C_6H_5-NH)_n-$, polyureas $(-R-NHCONH)_n$, and polyurethanes $-(CO-OR-OCO-NH-R'-NH)_n$, where the branched or terminal groups have free amino groups and the interior amine groups are also available.

Other polymers with free hydroxy groups will bind to salicylic acid by Van der Waals forces. Such polymers are polyvinyl vinyl alcohols $-(CH_2CHOH)-$, poly(2-HEMA), $(-CH_2-C(CH_3)(COOCH_2CH(OH)-)_n$, and poly(2-HPMA), $(-CH_2-C(CH_3)-(COOCH_2CH_2OH-)_n$ and $(-CH_2-C(CH_3)(COOCH_2CH(OH)CH_3)_n$. Such bonds are weaker, but may be enhanced by shared electrons across the aromatic ring of salicylic acid. Benzoyl peroxide will only form Van der Waals bonds with proteins or polymers. The complexation of benzoyl peroxide to proteins is achieved by sharing electrons across the peroxide moiety and the amido moiety in the polymer.

It is generally preferred that the complex be comprised of 40–50% by weight of anti-acne active and 50–60% by weight of carrier molecule. Ratios may vary depending on the effect desired. For example, in some cases it may be desired to have small levels of the anti-acne active deposited on the skin, in which case more appropriate ratios might range from 10–40% anti-acne active/60–90% carrier molecule, or vice versa.

It may be desired to encapsulate the complex to provide additional properties such as time release. Standard encapsulation methods are suitable, such as the methods disclosed in U.S. Pat. No. 5,194,262 which is hereby incorporated by reference.

THE DILUENT

The term "diluent" generally refers to a composition applied externally to the skin or hair of the human body for the purpose of cleansing, beautitizing, conditioning or protecting the body surface. A wide variety of diluents is suitable including but not limited to water-in-oil or oil-in-water emulsions in cream or lotion form, sunscreens, toners, astringents, facial make-ups, pressed or loose powder, skin cleansing compositions, and so on. In some cases it may be desired to apply the complex to the scalp to achieve keratolytic effects, so suitable diluents can also include shampoos and conditioners. In general, the cosmetically acceptable compositions of the invention contain about 0.1–30% of the complex and about 70–99.9% diluent. Preferably the compositions comprise about 0.1–10% complex and 90–99.9% diluent.

The complex may be incorporated into creams. Creams generally contain about 10–90% water and 10–90% oil. The oil may be low or high viscosity surface oils, volatile silicones, nonvolatile silicones, or amine functional silicones. Creams may also contain humectants, emollients, surfactants, emulsifiers, preservatives and fragrances. About 5–10% humectant, 5–20% emollient, and about 0.5

The diluent may be a lotion. Lotions are generally comprised of 20–80% oil and 10–80% water in an emulsion form. In addition, lotions may contain humectants, emollients, surfactants, fragrances, preservatives and so forth. About 5–10% humectant, about 5–20% emollient, and about 0.5–10% surfactant are: suggested.

The diluent may be a make-up. Make-ups generally comprise about 5–70% oil, 10–95% water, and about 5–40% pigment. In addition, the makeup may contain surfactants, silicones as part of the oil phase, humectants, emollients, preservatives, fragrances, etc. Generally 0.1 10% surfactant, 0.1–50% silicone, 0.1–20% humectant, 0.1–30% emollient, and 0.1–5% preservative is suggested. In the preferred embodiment of the invention the diluent is a make-up comprising 0.01–50% silicone, 30–60% water, 0.01–40% pigment, and 5–40% oil. The preferred composition may also comprise 0.1–20% humectant, 0.1–10% surfactant, and 0.1–5% preservative.

The make-up of the invention provides improved properties over the anti-acne make-ups currently available in that it does not change color or fade. Normally anti-acne actives, salicylic acid in particular, react with the iron oxide pigments commonly used in make-up. However, because the anti-acne active is bound to a carrier molecule, such reaction does not occur in the make-up composition of the invention.

The diluent may also be a blush, face powder, or other anhydrous make-up. Generally blushes contain about 5-75% pigment, 1-50% oil, and 1-20% wax. They may additionally contain one or more of 10-60% water, 0.5-30% surfactant, 1-10% humectants, 0.1-5% preservative, and 0.1-20% silicone. Anhydrous make-ups and concealers generally comprise one or more of 0.1-10% surfactant, 0.1-50% silicone, 0-20% humectant, 0.1-30% emollient, 0.1-50% pigme and 0.01-20% pigments. They may also contain one or more of 10-60% water, 0.5-30% surfactant, 1-10% humectants, 0.1-5% preservative, and 0.1-20% silicone.

The diluent may be a shampoo when it is desired to apply the anti-ache active (which also has keratolytic activity) onto the scalp. Suitable shampoo compositions contain 1-40% of a cleansing surfactant and 10-90% water. Preferably the surfactants are anionic or amphoteric. The shampoo may also contain any one of ingredients such as surfactants, colorants, preservatives, fragrance, emulsifiers, viscosity adjusters, and conditioning agents. If present, suitable ranges are 0.01-30% surfactant, 0.001-5% colorant, 0.001-5% preservative, 0.01-15% emulsifiers, 0.01-10% viscosity adjusters, and 0.1-20% conditioning agents.

The diluent may also be a hair conditioner. Suitable hair conditioning formulations include 10-95% water, 0.5-30% conditioning ingredients such as quaternary ammonium compounds or amphoteric polymers, proteins, etc., and 1-40% surfactants. Hair conditioners may also contain volatile or nonvolatile silicones; an amount of about 0.5-15% is suggested.

The diluent may be a toner which generally comprises about 0-85% alcohol, 0.01-5% surfactant, and 0.1-5% humectants, 0.1-85% water.

The diluent may also be pharmaceutical type vehicles such as ointments, gels or solutions. Suitable ointments are hydrophilic ointments (USP) or petroleum. Solutions are made by mixing the anti-ache active/carrier molecule complex in deionized water. Gels generally comprised about 1-90% water and about 1-90% of a suitable polymer such as polypropylene, etc.

Suitable emollients include glyceryl stearate, cetyl alcohol, stearyl alcohol, isopropyl stearate, stearyl stearate, isopropyl stearate, stearic acid, isobutyl pahnitate, isocetyl stearate, oleyl alcohol, sebacates, myristates, palmitates, squalenes, glyceryl monooleate, oleic acids, lanolin, acetylated lanolin alcohols, petroleum, mineral oils, palmitic acids, isostearyl neopentanoate, etc., as well as those set forth on pages 79-81 of the C.T.F.A. Cosmetic Ingredient Handbook, First Edition, 1988, which is hereby incorporated by reference.

Suitable humectants include glycerin, butylene glycol, propylene glycol, glucose, fructose, glucuronic acid, glueamine, glutamic acid, glycereth-7, glycereth-12, glycereth-26, histidine, honey lactose, mannitol methyl gluceth, sodium PCA PEG-10 propylene glycol, urea, xylitol, TEA-lactate, TEA-PCA, sucrose, sorbitol, PCA, sodium lactate, or mixtures thereof, as well as those set forth on page 75 of the C.T.F.A. Cosmetic Ingredient Handbook, First Edition, 1988, which is hereby incorporated by reference.

A variety of surfactants may be used in the diluent including amphoteric, anionic, cationic or nonionic surfactants. Suitable amphoteric surfactants include imidazolines, betaines, and amino acid salts. Suitable anionic surfactants include fatty acid soaps, salts of higher alkyl sulfates, n-acyl sarcosinates, salts of phosphates, sulfosuccinates salts, alkyl benzene sulfonates, salts of N-acyl glutamate, polyoxyethylene alkyl ether carboxylic acids, and so on. Cationic surfactants include alkyl trimethyl ammonium salts, alkyl pyridinium salts, alkyl quaternary ammonium salts, polyamine fatty acid derivatives, etc. Suitable anionic and amphoteric surfactants also include those designated as "cleansing agents" as set forth on pages 87-90 of the C.T.F.A. Cosmetic Ingredient Handbook, First Edition, 1988, which is hereby incorporated by reference. Nonionic surfactants include lipophilics such as sorbitan fatty acid esters, glycerol fatty acids, propylene glycol fatty acid esters; hydrophilics such as polyoxyethylene sorbitan fatty acid esters, polyoxyethylene glycerol fatty acid esters, polyoxyethylene fatty acid esters, polyoxyethylene alkyl ethers, pluronics, polyoxyethylene alkyl phenyl ethers, polyoxyethylene propylene glycol fatty acid esters, and so on. Examples of nonionic surfactants include those set forth in pages 90-94 of the C.T.F.A. Cosmetic Ingredient Handbook, First Edition, 1988, which is hereby incorporated by reference. Suitable cationic surfactants are set forth on page 97 of the C.T.F.A. Cosmetic Ingredient Handbook, First Edition, 1988, which is hereby incorporated by reference.

Suitable pigments include organic and inorganic pigments such as talc, mica, titanium dioxide, titanated mica, iron oxides, ultramarines, chromium oxides, carmine, D&C and FD&C colors and lakes, ferric and ferrous oxides, and so on, as set forth on pages 33 and 63 of the C.T.F.A. Cosmetic Ingredient Handbook, First Edition, 1988, which is hereby incorporated by reference.

Suitable preservatives include the ureas such as imidazolidinyl urea, diazolidinyl urea, the parabens, quaternium 15, benzyl alcohol, phenoxyethanol and so on.

Suitable waxes include beeswax, cetyl esters, carnauba, ceresin, microcrystalline, lanolin, paraffin, ozokerite, lanolin alcohol, acetylated lanolin, candelilla, cetyl alcohol, cocoa butter, petrolatum, hydrogenated castor oil, spermaceti, bran wax, capok wax, bayberry, hydrogenated jojoba oil, hydrogenated jojoba wax, hydrogenated rice bran wax, japan wax, jojoba butter, jojoba oil, mink, montan acid, montan, ouricury, shellac, etc.

Suitable silicones include cyclomethicone, dimethicone, stearoyl dimethicone, phenyl trimethicone, dimethiconol, dimethicone copolyols, etc.

In the preferred embodiment of the invention the anti-ache active/carrier molecule complex comprises 40-50% by weight plant protein (hydrolyzed vegetable protein) and 45-55% salicylic acid. The preferred diluent is a make-up or skin care product.

EXAMPLE 1

A concentrated solution of hydrolyzed vegetable protein in water is mixed with a 50% salicylic acid solution in ethanol. The resulting dispersion is mixed under shear. The mixture is allowed to stand for approximately 24 hours. Lyophilization is performed to yield a powdered material which comprises salicylic acid complexed to the hydrolyzed vegetable protein.

EXAMPLE 2

A water dispersion of about 50wt% polyamidoamine methacrylate crystals in water is prepared. A solution of 50% salicylic acid in ethanol is slowly added to the crystals with stirring for a half hour. The mixture is vacuum distilled to yield crystals having salicylic acid complexed thereto.

EXAMPLE 3

A concentrated dispersion of polyacrylamide in water is mixed with a 50% solution of salicylic acid in ethanol with high shear mixing. After 24 hours the resulting dispersion is lyophilized to yield crystals having salicylic acid complexed thereto.

EXAMPLE 4

A 50% solution of benzoyl peroxide in ethanol is mixed with a 25% solution of hydrolyzed vegetable protein. The mixture is allowed to stand for 24 hours. The mixture is then lyophilized to obtain a powder. The powder comprises hydrolyzed vegetable protein having benzoyl peroxide complexed thereto.

EXAMPLE 5

The salicylic complex of Example 1 was used to prepare a make-up composition as follows:

|  | w/w % |
|---|---|
| Salicylic acid/hydrolyzed veg. protein complex | 1.00 |
| Trisodium EDTA | 0.15 |
| Benzoic acid | 0.20 |
| 1,3-butylene glycol | 5.00 |
| Sodium polymethacrylate | 1.00 |
| Sorbitan sesquioleate | 0.50 |
| Simethicone | 0.15 |
| Glycerin | 5.00 |
| Magnesium aluminum silicate | 1.25 |
| Methyl paraben | 0.30 |
| Ethyl paraben | 0.10 |
| Polyethylene | 2.00 |
| Nylon 12 | 3.00 |
| Rutile titanium dioxide | 5.00 |
| Black iron oxide/talc | 0.53 |
| Red iron oxide/talc | 0.92 |
| Yellow iron oxide | 0.69 |
| Talc | 3.44 |
| Xanthan gum | 0.35 |
| Cyclomethicone | 15.00 |
| Diisopropyl linoleate | 3.50 |
| Polysorbate 20 | 1.00 |
| Water | 0.70 |
| Imidazolidinyl urea | 0.30 |

Water was heated to 60–65C. Salicylic acid/hydrolyzed vegetable protein complex, trisodium ETDA, benzoic acid, 1,3-butylene glycol, sodium polymethacrylate, sorbitan sesquioleate, simethicone, glycerin, magnesium aluminum-silicate, methyl paraben, ethyl paraben, polyethylene, nylon 12, the oxides, talc and xanthan gum were mixed in a colloid mill until all ingredients were dispersed. The mixture was then heated in a steam bath to 68–70° C. using a sweep mixer. Next combined were the oil phase ingredients: cyclomethicone, diisopropyl linoleate and polysorbate 20. The mixture was heated in a steam bath to 68–70° C. When the water and oil phases were at the same temperature, they were mixed with sweep action to form the emulsion. Sweep mixing was continued at the maintenance temperature for 15–20 minutes. The mixture was then removed from the bath and allowed to cool while maintaining mixing. The urea was added when the batch temperature reach 40–45° C.

EXAMPLE 6

An oil in water moisturizing lotion is made as follows:

|  | w/w % |
|---|---|
| Glyceryl stearate | 3.0 |
| PPG-10 lanolin ether | 0.5 |
| Mineral oil | 6.3 |
| Lanolin alcohol | 0.7 |
| Oleic acid | 2.7 |
| Isocetyl stearate | 10.00 |
| Triethanolamine | 1.3 |
| Carbomer 941 | 0.1 |
| Glycerin | 4.0 |
| Preservative | 0.4 |
| Salicylic acid/hydrolyzed vegetable protein complex | 5.00 |
| QS water | 100.00 |

The lotion was made by mixing into about 30 grams of water the remaining ingredients. The composition was emulsified and water added to 100 grams.

EXAMPLE 7

An oil-in-water moisturizing cream is made as follows:

|  | w/w % |
|---|---|
| Glyceryl stearate | 5.0 |
| Cetyl alcohol | 2.0 |
| Stearyl alcohol | 2.0 |
| Isopropyl stearate | 4.0 |
| Mineral oil | 12.0 |
| Polysorbate 60 | 1.0 |
| Glycerin | 8.0 |
| Xanthan gum | 0.25 |
| Preservative | 0.60 |
| Salicylic acid/hydrolyzed vegetable protein complex | 5.00 |
| Water QS | 100.00 |

The ingredients were combined and mixed to emulsify.

EXAMPLE 8

An anhydrous makeup with salicylic acid was made as follows:

|  | w/w % |
|---|---|
| Stearoyl dimethicone | 12.00 |
| Phenyl trimethicone | 16.00 |
| Octyldodecanol | 12.00 |
| Dimethicone | 4.00 |
| BHA | 0.10 |
| Phenoxyethanol | 0.70 |
| Titanium dioxide | 15.00 |
| Black iron oxide/talc | 0.26 |
| Red iron oxide/talc | 2.00 |
| Yellow iron oxide/talc | 5.00 |
| Talc | 6.94 |
| Lecithin treated mica | 6.00 |
| Hydrogenated coco glycerides | 10.00 |
| Ceresin wax | 1.00 |
| Tribehenin | 8.00 |
| Salicylic acid/hydrolyzed vegetable protein | 1.00 |

|  | w/w % |
|---|---|
| protein complex | |

All ingredients except the complexed salicylic acid/protein was mixed in a steam bath until waxes were molten. The entire batch was roller milled until pigments were dispersed. The mixture was then returned to the steam bath anti the salicylic acid complex was added. The batch was prop mixed until cooled to room temperature.

EXAMPLE 9

An anhydrous concealer stick was made as follows:

|  | w/w % |
|---|---|
| Ceresin wax | 15.00 |
| Carnauba | 2.00 |
| Wax blend | 4.00 |
| Microcrystalline wax | 2.50 |
| Ester blend | 30.00 |
| Prepolymer 2 | 10.00 |
| Octyldodecanol | 13.00 |
| Sorbitan sesquioleate | 1.00 |
| Octyldodecyl stearoyl stearate | 2.00 |
| Bismuth oxychloride | 2.00 |
| Polymethylmethacrylate | 3.00 |
| Talc | 5.70 |
| Lecithin treated black I.O. | 1.00 |
| Lecithin treated red I.O. | 2.00 |
| Lecithin treated yellow I.O. | 5.00 |
| Phenoxyethanol | 0.70 |
| BHA | 0.10 |
| Salicylic acid/hydrolyzed vegetable protein complex | 1.00 |

All ingredients except the salicylic acid/protein complex were mixed in a steam bath until waxes were molten. The entire batch was roller milled until pigments were dispersed. The batch was returned to the steam bath and the salicylic acid complex was added. The batch was prop mixed until it cooled to room temperature.

EXAMPLE 10

A shampoo composition was made as follows:

|  | w/w % |
|---|---|
| Ammonium lauryl sulfate | 10.00 |
| Cocamide diethanolamine | 4.00 |
| Cocamidopropyl betaine | 4.00 |
| Ammonium chloride | 0.80 |
| Citric acid | 0.10 |
| Salicylic acid/hydrolyzed vegetable protein complex | 5.00 |
| Water QS | 100.00 |

EXAMPLE 11

A creme rinse hair conditioner was made as follows:

|  | w/w % |
|---|---|
| Stearalkonium chloride | 2.0 |
| Cetyl alcohol | 1.0 |
| Stearyl alcohol | 0.5 |
| Ceteareth 20 | 2.0 |
| Xanthan gum | 0.5 |
| Citric acid | 0.3 |

|  | w/w % |
|---|---|
| Dimethicone | 0.2 |
| Salicylic acid/hydrolyzed vegetable protein complex | 5.00 |
| Water QS | 100.00 |

EXAMPLE 12

A toner composition was made as/follows:

|  | w/w % |
|---|---|
| Polysorbate 20 | 1.0 |
| Ethyl alcohol | 50.00 |
| Perfume | 8.00 |
| Salicylic acid/hydrolyzed vegetable protein complex | 10.00 |
| Water QS | 100.00 |

EXAMPLE 13

A cleansing cream was made as follows:

|  | w/w % |
|---|---|
| Mineral oil | 20.00 |
| Beeswax | 2.00 |
| Polysorbate 40 | 8.00 |
| PEG 20 sorbitan beeswax | 2.00 |
| Stearic acid | 10.00 |
| Petrolatum | 4.00 |
| Sorbitol | 5.00 |
| Perfume | 1.00 |
| Preservative | 0.50 |
| Salicylic acid/hydrolyzed veg. protein complex | 10.00 |
| Water QS | 100.00 |

WE CLAIM:

1. A cosmetically acceptable composition with keratolytic activity comprising:
   0.01–75% by weight of a keratolytic compound complexed to a carrier molecule having at least one hydroxyl or amino group, 75–99.9% by weight of a diluent.

2. The composition of claim 1 wherein the keratolytic compound is resorcinol, benzoyl peroxide, salicylic acid, or mixtures thereof.

3. The composition of claim 2 wherein the carrier molecule is hydrolyzed vegetable protein, hydrolyzed animal protein, a branched polyamidoamine, a polyamide, polyaniline, polyurea, polyurethane, polyvinyl alcohol derivative, or mixtures thereof.

4. The composition of claim 3 wherein the carrier molecule is complexed to the keratolytic compound by ionic, covalent, or Van der Waals bonding.

5. The composition of claim 4 wherein the diluent is a cream, lotion, make-up, blush, skin cleanser, sunscreen, toner, astringent, or powder.

6. The composition of claim 4 wherein the complex comprises 10–40% by weight of keratolytic compound and 60–90% by weight of carrier molecule.

7. The composition of claim 6 comprising 0.01–20% by weight of the total composition of the keratolytic ingredient/carrier molecule complex and 80–99.9% by weight of the total composition of diluent.

8. The composition of claim 7 wherein the diluent is a makeup containing 5–70% oil, 10–95% water, and 5–40% pigment.

9. The composition of claim 8 wherein the makeup comprises 0.01–50% silicone, 30–60% water, 0.01–40% pigment and 5–40% oil.

10. The composition of claim 9 wherein the make-up additionally comprises 0.1–20% humectant, 0.1–10% surfactant, and 0.1–5% preservative.

11. A method for treating *acne vulgaris* comprising:
   a) complexing a keratolytic compound to a carrier molecule having at least one hydroxyl or amino group,
   b) adding an effective amount of said complex of (a) to a cosmetically acceptable diluent,
   c) applying the composition of (b) to a subject's face at least once per day.

12. The method of claim 11 wherein the keratolytic compound is an salicylic acid.

13. The method of claim 12 wherein the diluent is a make-up.

14. The method of claim 13 wherein the carrier molecule is hydrolyzed vegetable protein.

15. The method of claim 14 wherein the salicylic acid is ionically bound to hydrolyzed vegetable protein.

16. The method of claim 15 wherein the make-up comprises 5–70% oil, 1.0–95% water, and 5pigment.

17. The composition of claim 16 wherein the make-up comprises 0.01–50% silicone, 30–60% water, 0.01–40% pigment and 5–40% oil.

18. A facial make-up composition having anti-keratolytic activity comprising:
   0.01–50% silicone
   0.01–10% of salicylic acid ionically bound to hydrolyzed vegetable protein,
   0.01–40% pigment, and
   5–40% oil,
   wherein when the make-up composition is applied to the face the ionic bond between the salicylic acid and hydrolyzed vegetable protein is ruptured and the tree salicylic acid is absorbed onto the skin.

19. The composition of claim 18 further comprising 0.1–10% surfactant, 0.1–20% humectant, 0.1–30% emollient, or mixtures thereof.

20. The composition of claim 19 wherein the silicone is a mixture of volatile and nonvolatile silicone.

* * * * *

UNITED STATES PATENT AND TRADEMARK OFFICE
CERTIFICATE OF CORRECTION

PATENT NO. : 5,449,519

DATED : September 12, 1995

INVENTOR(S) : Wolf et al.

It is certified that error appears in the above-identified patent and that said Letters Patent is hereby corrected as shown below:

On the front page of the patent, in the Abstract Section, after "A cosmetically acceptable composition with anti-" delete "ache" and insert therefor --acne--.

In column 1, line 14, after "The pathology of" delete "ache" and insert therefor --acne--.

In column 1, line 34, after "effectively suppresses the" delete "ache" and insert therefor --acne--.

In column 1, line 35, after "bacillus" delete "propionibacterium aches" and insert therefor --Propionibacterium acnes--.

In column 1, line 36, after " casual role in" delete "ache" and insert therefor --acne--.

In column 2, line 5, after "also have anti-" delete "ache" and insert therefor --acne--.

In column 2, line 8, after "the keratolytic" delete "con,pound" and insert therefor --compound--.

In column 3, line 6, after "and the anti-" delete "ache" and insert therefor --acne--.

In column 3, line 11, after "ionically bound to the" delete "tree" and insert therefor --free--.

In column 5, line 23, after "apply the anti-" delete "ache" and insert therefor --acne--.

In column 5, line 47, after "made by mixing the anti-" delete "ache" and insert therefor --acne--.

UNITED STATES PATENT AND TRADEMARK OFFICE
CERTIFICATE OF CORRECTION

PATENT NO. : 5,449,519

DATED : September 12, 1995

INVENTOR(S) : Wolf et al.

It is certified that error appears in the above-identified patent and that said Letters Patent is hereby corrected as shown below:

In column 5, line 63, after "acid," delete "glueamine" and insert therefor --glucamine--.

In column 6, line 58, after "anti-" delete "ache" and insert therefor --acne--.

In column 12, line 2, delete 1.0-95% water, insert --10-95% water--; and delete "5pigment" and insert therefor --5-40% pigment--.

In column 12, line 16, after "the" delete "tree" and insert therefor --free--.

Signed and Sealed this

Ninth Day of July, 1996

BRUCE LEHMAN

*Attest:*

*Attesting Officer*        Commissioner of Patents and Trademarks

(12) REEXAMINATION CERTIFICATE (4327th)
United States Patent
Wolf et al.

(10) Number: US 5,449,519 C1
(45) Certificate Issued: May 1, 2001

(54) COSMETIC COMPOSITIONS HAVING KERATOLYTIC AND ANTI-ACNE ACTIVITY

(75) Inventors: Barbara A. Wolf, Scarsdale, NY (US); Florence Snyder, Sayreville, NJ (US)

(73) Assignee: Revlon Consumer Products Corporation, New York, NY (US)

Reexamination Requests:
No. 90/005,134, Oct. 1, 1998
No. 90/005,448, Aug. 12, 1999

Reexamination Certificate for:
Patent No.: 5,449,519
Issued: Sep. 12, 1995
Appl. No.: 08/288,098
Filed: Aug. 9, 1994

Certificate of Correction issued Jul. 9, 1996.

(51) Int. Cl.$^7$ .................................................. A61K 7/48
(52) U.S. Cl. .................. 424/401; 424/70.1; 424/70.8; 424/70.11; 424/70.14; 424/70.17; 424/DIG. 5; 424/70.12; 514/159; 514/845; 514/859; 514/880; 514/881; 514/939
(58) Field of Search ................................... 424/401, 70.1, 424/70.8, 70.11, 70.14, 70.17, 78.02, DIG. 5, 70.12; 514/159, 859, 880, 881, 939

(56) References Cited

U.S. PATENT DOCUMENTS 3,954,989 * 5/1976 Mecca .................................. 424/273
4,416,873 * 11/1983 Puchalski et al. .................... 424/177
4,917,891   4/1990 Kaufman et al. ..................... 424/401
4,946,870   8/1990 Partain, III et al. ................. 514/777
5,122,370 *  6/1992 Merianos et al. ................. 424/78.05
5,338,532   8/1994 Tomalia et al. ...................... 424/149
5,631,244   5/1997 Galons et al. ......................... 514/58

FOREIGN PATENT DOCUMENTS 0 038 246 A1    10/1981  (EP).
    0038246    10/1981  (EP).
0 624 599 A2 * 11/1994  (EP).
    0624599    11/1994  (EP).
  2 105 727    3/1983  (GB).
WO 90/14836 * 12/1990  (WO).
WO 95/04537 *  2/1995  (WO).

OTHER PUBLICATIONS

Encyclopedia of Chemical Technology, John Wiley & Sons, vol. 7, pp. 598, (1993).

Kirk Othmer Encyclopedia of Chemical Technology, 4$^{th}$ Ed., vol. 7, 1993, p. 598.

* cited by examiner

Primary Examiner—James M. Spear

(57) ABSTRACT

A cosmetically acceptable composition with anti-acne or keratolytic activity comprising: 0.01 to 25% by weight of a keratolytic compound complexed to a carrier molecule, 75–99.95 % by weight of a diluent.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–2, 4–5 and 12–13 are cancelled.

Claims 3, 6, 8, 11, 14, 16 and 18 are determined to be patentable as amended.

Claims 7, 9, 10, 15, 17, 19 and 20, dependent on an amended claim, are determined to be patentable.

3. [The composition of claim 2 wherein] *A cosmetically acceptable composition with keratolytic activity comprising:*
   *0.01 to 25% by weight of a complex of a keratolytic compound complexed to a carrier molecule by covalent, ionic or van Der Waals bonding, the carrier molecule having at least one hydroxyl or amino group, wherein the keratolytic compound is resorcinol, benzoyl peroxide, salicylic acid, or mixtures thereof and* the carrier molecule is hydrolyzed vegetable protein, hydrolyzed animal protein, [a branched polyamidoamine, a polyamide,] polyaniline, polyurea, polyurethane, polyvinyl alcohol derivative, or mixtures thereof, *and 75–99.9% by weight of a diluent which is a cream, lotion, make-up, blush, skin cleanser, sunscreen, toner, astringent, or powder.*

6. The composition of claim [4] *3* wherein the complex comprises [10–40] *10–50%* by weight of keratolytic compound and [60–90] *50–90%* by weight of carrier molecule.

8. The composition of claim 7 wherein the diluent is a makeup containing 5–70% oil, [10–95] *10–90%* water, and 5–40% pigment.

11. A method for treating acne vulgaris comprising:
   a) complexing a keratolytic compound *which is salicylic acid* to a carrier molecule [having at least one hydroxyl or amino group] *which is hydrolyzed animal or vegetable protein,*
   b) adding an effective amount of said complex of (a) to a cosmetically acceptable diluent, *wherein the diluent is a cream, lotion, makeup, blush, skin cleanser, sun screen, astringent, shampoo or conditioner, and*
   c) applying the composition of (b) to a subject's face at least once per day.

14. [The method of claim 13 wherein the] *A method for treating acne vulgaris comprising:*
   *a) complexing a salicylic acid to a* carrier molecule [is] *of* hydrolyzed vegetable protein,
   *b) adding an effective amount of said complex of (a) to a cosmetically acceptable makeup, and*
   *c) applying the composition of (b) to a subject's face at least once per day.*

16. The method of claim 15 wherein the make-up comprises 5–70% oil, [1.0–95] *10–90%* water, and 5–40% pigment.

18. A facial make-up composition having anti-keratolytic activity comprising:
   0.01–50% silicone
   0.01–10% of salicylic acid ionically bound to hydrolyzed vegetable protein,
   0.01–40% pigment, and
   5–40% oil,
   wherein when the make-up composition is applied to the face the ionic bond between the salicylic acid and hydrolyzed vegetable protein is ruptured and [the] free salicylic acid is absorbed onto the skin.

* * * * *